(12) United States Patent
Bertsch

(10) Patent No.: US 8,624,167 B2
(45) Date of Patent: Jan. 7, 2014

(54) DEVICE FOR MAKING A MUFFLE

(75) Inventor: Diethard Bertsch, Göfis (AT)

(73) Assignee: Ivoclar Vivadent AG, Schaan (LI)

( * ) Notice: Subject to any disclaimer, the term of this patent is extended or adjusted under 35 U.S.C. 154(b) by 1069 days.

(21) Appl. No.: 12/383,673

(22) Filed: Mar. 26, 2009

(65) Prior Publication Data

US 2009/0250450 A1    Oct. 8, 2009

(30) Foreign Application Priority Data

Apr. 8, 2008  (DE) .......................... 10 2008 017 784

(51) Int. Cl.
*F27B 5/14*   (2006.01)
*A61C 8/00*   (2006.01)

(52) U.S. Cl.
USPC ........... 219/390; 219/494; 219/524; 219/525; 219/759; 264/16; 264/17; 264/18; 264/19; 264/20; 433/18; 433/32; 433/201.1; 433/202.1; 433/213; 433/215; 433/218; 433/223

(58) Field of Classification Search
CPC ........ A61C 13/00; A61C 13/08; A61C 13/20; A61C 13/34; B21J 1/06; F27B 5/14
USPC .......... 219/390, 525, 524, 494, 759; 432/212, 432/32; 264/16–20, 297.9; 433/18, 32, 433/201.1, 202.1, 213, 215, 218, 223; 106/35
See application file for complete search history.

(56) References Cited

U.S. PATENT DOCUMENTS

| | | | | |
|---|---|---|---|---|
| 589,048 A | * | 8/1897 | Timme | 219/390 |
| 714,373 A | * | 11/1902 | Hewett et al. | 219/390 |
| 781,762 A | * | 2/1905 | Bosworth | 219/390 |
| 787,584 A | * | 4/1905 | Matteson | 219/390 |
| 820,025 A | * | 5/1906 | Steinecke | 219/390 |
| 849,335 A | * | 4/1907 | Markwitz | 219/390 |
| 1,358,220 A | * | 11/1920 | Ledig | 219/390 |

(Continued)

FOREIGN PATENT DOCUMENTS

| | | |
|---|---|---|
| CA | 2548760 | 7/2005 |
| DE | 539734 | 12/1931 |

(Continued)

OTHER PUBLICATIONS http://dictionary.reference.com/browse/Parallel.

*Primary Examiner* — Henry Yuen
*Assistant Examiner* — Brett Spurlock
(74) *Attorney, Agent, or Firm* — Ann M. Knab; Thad McMurray

(57) ABSTRACT

A device for making a muffle, with which dental restoration parts can be produced with the aid of an embedding compound, at least one press blank and a pressing device, the device having a muffle base, a tubular sleeve surrounding the muffle base and at least one muffle insert which is arranged on the muffle base and can be separated from it. At least two cylindrical press-channel forming elements (16, 18, 20) extend parallel to one another and spaced apart from one another from a flat-formed portion of the muffle insert (12), which can be burned out at least with respect to the forming elements, which elements are formed in a closed manner, and in particular with thin walls, at least on one free end face opposite from the flat-formed portion (14).

19 Claims, 4 Drawing Sheets

(56) References Cited

U.S. PATENT DOCUMENTS

| | | | |
|---|---|---|---|
| 1,399,638 A * | 12/1921 | Marx | 432/64 |
| 1,534,592 A * | 4/1925 | Houck | 219/390 |
| 1,644,107 A * | 10/1927 | Pervier A et al. | 219/390 |
| 1,654,026 A * | 12/1927 | Veatch | 249/54 |
| 1,676,677 A * | 7/1928 | Axelrod | 219/390 |
| 2,447,369 A * | 8/1948 | Schweitzer | 432/262 |
| 2,787,457 A * | 4/1957 | Bogdan | 219/390 |
| 2,885,197 A * | 5/1959 | Cope et al. | 432/38 |
| 3,109,911 A * | 11/1963 | Kremer | 219/390 |
| 3,128,325 A * | 4/1964 | Keaty et al. | 373/111 |
| 4,208,573 A * | 6/1980 | Risse | 219/411 |
| 4,627,136 A * | 12/1986 | Kreylos et al. | 29/896.1 |
| 4,734,173 A * | 3/1988 | Walter et al. | 205/660 |
| 4,771,162 A * | 9/1988 | Schatz et al. | 219/400 |
| 4,779,848 A * | 10/1988 | Brimm et al. | 266/259 |
| 4,904,348 A * | 2/1990 | Domes et al. | 205/67 |
| 5,095,192 A * | 3/1992 | McEntire et al. | 219/402 |
| 5,227,602 A * | 7/1993 | Kuhn | 219/69.17 |
| 5,655,592 A * | 8/1997 | Sullivan | 164/456 |
| 5,824,078 A * | 10/1998 | Nelson et al. | 623/66.1 |
| 5,858,417 A * | 1/1999 | Bosshart | 425/192 R |
| 5,868,749 A * | 2/1999 | Reed | 606/76 |
| 6,132,472 A * | 10/2000 | Bonutti | 623/23.72 |
| 6,180,922 B1 * | 1/2001 | Rohner et al. | 219/390 |
| 6,328,568 B1 * | 12/2001 | Sato | 433/223 |
| 6,361,408 B1 * | 3/2002 | Bleier | 451/45 |
| 6,484,791 B1 * | 11/2002 | Vidal | 164/113 |
| 6,485,849 B2 * | 11/2002 | Petticrew | 428/697 |
| 6,648,646 B2 * | 11/2003 | Sato | 433/223 |
| 6,659,165 B1 * | 12/2003 | Miyake et al. | 164/495 |
| 6,696,073 B2 * | 2/2004 | Boyce et al. | 424/422 |
| 6,730,246 B2 * | 5/2004 | Price et al. | 264/17 |
| 6,740,267 B1 * | 5/2004 | Sekino et al. | 264/19 |
| 7,118,085 B2 | 10/2006 | Foser et al. | |
| 7,507,080 B2 | 3/2009 | Helmberger | |
| 7,704,421 B2 * | 4/2010 | Cadario et al. | 264/20 |
| 7,845,924 B2 * | 12/2010 | Cadario et al. | 425/130 |
| 2002/0179586 A1 * | 12/2002 | Wengert et al. | 219/390 |
| 2003/0226475 A1 * | 12/2003 | Stern | 106/38.9 |
| 2004/0053200 A1 * | 3/2004 | Kato et al. | 433/215 |
| 2004/0108610 A1 * | 6/2004 | Foser et al. | 264/16 |
| 2005/0175949 A1 * | 8/2005 | Grunenfelder et al. | 432/120 |
| 2005/0204796 A1 * | 9/2005 | Foser | 72/342.8 |
| 2006/0151480 A1 * | 7/2006 | Zubler | 219/635 |
| 2006/0175316 A1 * | 8/2006 | Smith | 219/390 |
| 2006/0188837 A1 * | 8/2006 | Helmberger et al. | 433/34 |

FOREIGN PATENT DOCUMENTS

| | | |
|---|---|---|
| DE | 9001740 U | 5/1990 |
| DE | 10241857 | 4/2003 |
| DE | 10325660 | 1/2005 |
| DE | 20 2005 001344 U1 | 6/2005 |
| DE | 20 2005 003014 U1 | 6/2005 |
| JP | 2005279087 A | 10/2005 |
| WO | WO 2005/061142 A1 | 7/2005 |

* cited by examiner

DEVICE FOR MAKING A MUFFLE

CROSS-REFERENCE TO RELATED APPLICATIONS

This application claims foreign priority benefits under 35 U.S.C. §119(a)-(d) from German patent application ser. no. P 10 2008 017 784.9 filed Apr. 8, 2008.

TECHNICAL FIELD

The invention relates to a device for making a muffle, with which dental restoration parts can be produced with the aid of an embedding compound, at least one press blank and a pressing device.

BACKGROUND OF THE INVENTION

It has long been known to use devices to help simplify the production of suitable molds for the production of dental restoration parts. For example, it is known according to DE 539 734 to use what is known as a melting crucible former for forming the lining material, which has a high content of gypsum and to that extent corresponds to a muffle, a substantially conical base plate and a lining ring being used there, the latter as a sleeve.

This solution already allows a mold cavity, which is initially modelled in wax as a positive mold, to be created in the muffle, and then serve after curing as a pressing space for the dental restoration.

A comparatively much improved device for making a muffle is known from DE 900 17 40 U1. In the case of this solution, a central mold attachment is provided, which projects from an end wall part and allows models to be grown on its tooth supporting surface. After hardening of the muffle, to provide the dental restoration it is necessary for the mold attachment together with the end wall part to be pulled off, so that a certain strength is necessary there to ensure the desired clean separation of muffle and wax.

Specifically in the case of a cylindrical construction of the mold attachment, this solution requires a certain strength of the mold attachment, and consequently also a comparatively great wall thickness of the mold attachment, which is for example much greater than the wall thickness of the sleeve which surrounds the muffle.

To facilitate the pulling out of such a mold attachment, the mold attachment may be turned, and at the same time pulled out. This also facilitates the detachment without impairing or damaging the muffle.

However, such turning is only possible in the case of circular-symmetrical forms of the mold attachment, and also only when only one mold attachment is provided. In this connection, it has also been proposed to create special pulling devices for the mold attachments that are connected to pulling tools. Although a mold attachment can be removed from the muffle with such a pulling device, the comparatively high forces that must overcome the adhesion between the mold attachment and the muffle put at risk the intactness of the muffle, so that this solution has not been adopted.

Furthermore, it has also been proposed to design such mold attachments not in a cylindrical manner but in a slightly conical manner, or possibly even slightly spherical, to facilitate demolding. Although this can assist demolding, this solution has also not been adopted, since it is not possible in this way to use the feed channel created in the muffle as a press channel, because otherwise, in view of the conical form, the cylindrical press blank deviates to the side, which leads to serious blockages and in any event means that it is not ensured that dental material in a semifinished state will pass by the sides of the press ram, so that the mold cavity is not completely filled.

Furthermore, various other attempts have been undertaken to improve the making of muffles. For instance, it has been attempted to increase the diameter, or at least the cross-sectional area, of a press channel, in order also to create larger dental restoration parts, or possibly to create a number of dental restoration parts. However, an increase in the cross-sectional area also requires a correspondingly increased pressing pressure, so that then the wall thickness of the muffle also has to be increased to withstand the increased pressing pressure. Moreover, it has been found that an increased pressing pressure more easily leads to "compression" of the muffle, and consequently to reduction of the dimensional accuracy, so that, all in all, increasing the cross-sectional area of the press channel has not proven to be a promising prospect.

OBJECTS AND SUMMARY OF THE INVENTION

Therefore, the invention is based on the object of simplifying and optimizing the production of dental restorations by means of muffles, and of providing for this purpose a correspondingly suitable device.

According to the invention, the "parallelization" of the press channels results in comparatively little loading of the muffle in spite of good pressing performance and a good pressing displacement per unit of time. In a way similar to how a grid can be subjected to greater structural loading than a forming element with a single large hole, according to the invention the muffle is quite pressure-resistant without the wall thickness having to be increased appreciably. Here, the invention benefits from the fact that flaking off of the muffle can in principle only take place toward the outside, so that the inwardly acting compressive forces compensate for one another.

According to the invention, specifically a muffle with quite closely spaced-apart press channels can be created particularly favorably with a special flat-formed muffle insert from which press-channel forming elements protrude.

The press-channel forming elements are particularly thin-walled, so that they can also be readily burned out if they cannot be pulled off from the gypsum in the manner of a skin. The heating above the vaporization point of the material for the press-channel forming elements provides the assurance that the press-channel forming element is removed without leaving any residual material, so that the press channel is available exactly in the desired form.

If need be, the press-channel forming elements may be created together with a flat-formed portion of the muffle insert, that is to say in one piece, which is then designed with preference likewise in such a way that it can be burned out. The free end face opposite from the flat-formed portion is formed in a closed manner and receives the positive mold of the dental restoration formed in wax. Provided there in a way that is known per se are growing channels, which make it possible for the molten dental ceramic to be advanced into the mold cavity.

According to the invention, it is ensured by the creation of exactly parallel press channels through the cylindrical press-channel forming elements, which by allowing themselves to be burned out without leaving any residual material ensure corresponding forms, that the press rams for the parallel pressing of the blanks are also guided with little lateral play, but precisely, so that good pressing results can be expected.

According to the invention, a number of pellets or press blanks of comparatively high weight of the pressing ceramic of at least 20 grams, but if need be even up to 40 grams, which corresponds to a wax weight of 12 grams, can be pressed in parallel. This is so because, according to the invention, it is particularly favorable that the dental restorations grown on the end face of the forming elements according to the invention that are free according to the invention can also be connected to one another, so that it is possible according to the invention to create dental ceramics that are much larger and also technically optimized in terms of pressing.

According to the invention, in this way it is now possible for demanding restoration tasks to be performed in one operation, and consequently much more efficiently than in the case of the previously known muffles, without the feared "compression" of the muffle material that inevitably occurs at high pressures adversely affecting the accuracy of the restoration result.

It goes without saying that the muffle wall thickness, and consequently the size of the muffle, can be adapted to requirements within wide ranges. Typically, with parallel pressing of, for example, six press channels, the muffle will have a much greater diameter than for example in the case of the solution according to DE 900 17 40 U1, but by no means six times the diameter. Altogether, the parallel processing has to this extent the effect not only of significantly reducing the cycle time of the working process, but in particular also of saving muffle material, provided that parallel creation of a number of dental restorations takes place, as is possible according to the invention.

The invention is not restricted to the one-piece creation of the press-channel forming elements with a flat-formed portion of the muffle insert. For example, if need be, the forming elements may also be partially omitted, and the "hole" remaining as a result in the flat-formed portion of the muffle insert is covered at once, for example with a corresponding plate. By means of corresponding casting inserts, which reduce the effective diameter of the muffle, it is possible to form a muffle of reduced size, with for example only two press-channel forming elements, which can however if need be increased again to the maximum number.

According to the invention, it is also particularly favorable that the muffle insert is supported by a muffle base, with preference in the flat-formed portion. The muffle base is a reusable part and securely supports the muffle insert from below, so that, when the gypsum-like compound is poured into the sleeve, the flat-formed portion of the muffle insert does not buckle downward.

According to the invention, it is particularly favorable if the press channels created are spaced apart from one another much less than they are spaced away from the outer wall of the muffle. The spacing between the individual press channels may be reduced for example to just 5 mm, while the spacing with respect to the outside diameter of the muffle, that is to say the "wall thickness" of the muffle, may for example be more than 2 cm. It is particularly favorable if the flat-formed portion of the muffle insert is securely mounted on the muffle base, for example by positive engagement, but can nevertheless be separated.

With preference, the quite thin-walled muffle insert can be fastened by means of a latching connection on a location of the muffle insert that is spaced away from the flat-formed portion.

With preference, the muffle insert is thin-walled, but hard and to this extent inelastic. For example, its Shore hardness according to DIN 53505 or DIN 7868 may be much greater than that of natural rubber and be for example more than 70° A, in particular 75° A. This configuration makes it possible to provide alignment of the press channels that is precise in spite of thin walls, with exactly parallel side walls.

EPM, that is to say ethylene-propylene rubber, with a hardness of 85° A, comes into consideration for example, while it goes without saying that, with preference, no fillers should be contained. Polyethylene raw materials with a hard formulation are particularly suitable for this in principle, typically burning without leaving any residual material (cf. also EP 170 40 01).

According to the invention, it is provided that the wall thickness of the forming elements substantially corresponds to the wall thickness of the flat-formed portion or is up to 90 percent smaller than it and wherein the wall thickness of each forming element corresponds to at least 0.03 times the diameter, with preference at most 0.1 times the diameter, of a forming element. In a further advantageous refinement, it is provided that the muffle insert is formed as a self-supporting or non-self-supporting, one-piece disposable part. In a further advantageous refinement, it is provided that the muffle base stiffens the muffle insert, at least in the region of the flat-formed portion, and the forming elements of the muffle insert are supported on the muffle base. In a further advantageous refinement, it is provided that at least one feed channel for at least one dental restoration part can be attached on the end face opposite from the flat-formed portion. In a further advantageous refinement, it is provided that the smallest spacing between two cylindrical forming elements is at least 0.5 mm. In a further advantageous refinement, it is provided that the flat-formed portion of the muffle insert can be detachably connected to the muffle base. In a further advantageous refinement, it is provided that the flat-formed portion of the muffle insert can be positively connected to the muffle base, in particular to a downwardly extending collar. In a further advantageous refinement, it is provided that the muffle insert protrudes into at least one depression of the muffle base.

In a further advantageous refinement, it is provided that a projection of the muffle insert protrudes into at least one blind-hole bore of the muffle base or at least partially into a groove on the muffle base formed at least partially around it.

In a further advantageous refinement, it is provided that the muffle base is formed in a radially elastic manner, at least in the region of the groove.

In a further advantageous refinement, it is provided that the sleeve fitted onto the muffle base fixes the part of the flat-formed portion that protrudes into the groove on the muffle base, in particular in the groove of the muffle base.

In a further advantageous refinement, it is provided that the outside diameter of the flat-formed portion corresponds at most to the inside diameter of the sleeve.

In a further advantageous refinement, it is provided that the outside diameter of the forming elements is 6 mm to 20 mm.

In a further advantageous refinement, it is provided that the muffle insert has a number of forming elements, which are arranged in a circular or square or cruciform or rectangular or arcuate or elliptical manner or in a row, in particular in the inner half of the diameter of the muffle insert.

In a further advantageous refinement, it is provided that the forming elements are formed with different heights and/or have different diameters.

In a further advantageous refinement, it is provided that the forming elements have a circular form or an outer contour other than of a circular form.

In a further advantageous refinement, it is provided the forming elements have different outer forms.

In a further advantageous refinement, it is provided that the hollow space of the forming elements can be fitted with elements, in particular pin-shaped elements, the diameter of which corresponds to the inside diameter of the forming element and which are supported on the muffle base.

Further advantages, details and features emerge from the following description of an exemplary embodiment on the basis of the drawing, in which:

DETAILED DESCRIPTION

Figure 1:
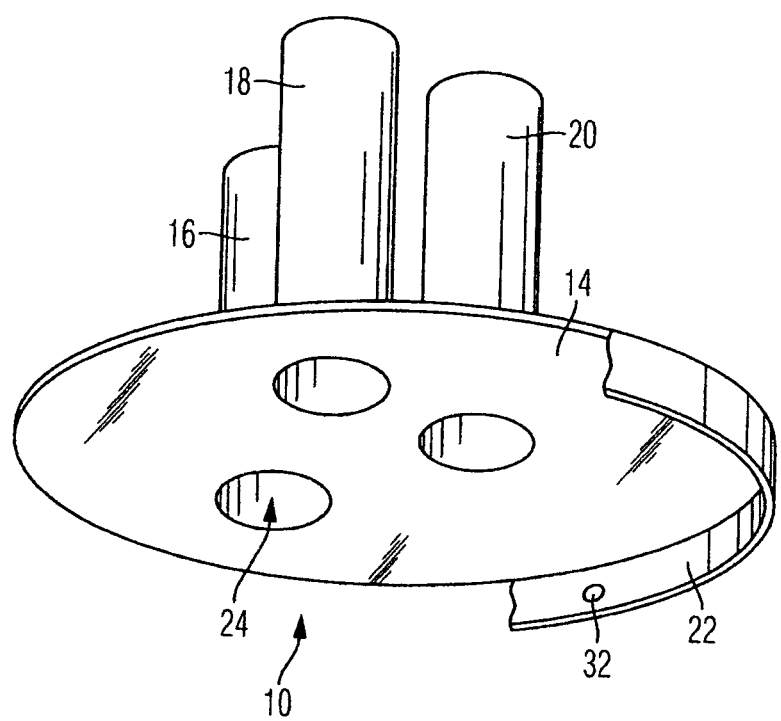
FIG. 1 shows a schematic perspective view of a muffle insert for use in a device according to the invention, in a first embodiment.

The device 10 represented in FIG. 1 has, apart from other parts, a muffle insert 12. The muffle insert 12 comprises a flat-formed portion 14 and press-channel forming elements, three press-channel forming elements 16, 18 and 20 being provided in the exemplary embodiment represented. However, it is also readily possible in a modified configuration of the device to use any other number of press-channel forming elements, for instance in the range from two to ten forming elements.

The forming elements 16 to 20 are centrally arranged, so that they extend around the center of the circular flat-formed portion 14. The spacing between the forming elements 16 and the edge of the flat-formed portion 14 is much greater, for example by a factor of 2 to 20, than the spacing of the forming elements from one another.

The flat-formed portion 14 is surrounded by a collar 22, which extends downward in the manner of an apron, to be precise by approximately one tenth of the diameter of the muffle insert. A collar 22 increases the dimensional stability of the muffle insert 12.

In the exemplary embodiment represented, the muffle insert is formed in one piece by the flat-formed portion 14, the forming elements 16-20 and the collar 22, to be precise as a disposable part made of a comparatively thin-walled plastic. It goes without saying that, instead of this, the forming elements 16-20, may also be detachably mounted on the flat-formed portion 14, it being possible for any suitable coupling to be created there.

It is also possible in principle to provide a muffle insert with for example six forming elements. If fewer than six dental restoration parts are produced, or if fewer than six forming elements 16 to 20 are required, the forming elements may then at once be cut off directly at their attachment to the flat-formed portion 14, for example with a knife. The opening exposed in this way can then be covered with a suitable covering plate, which overlaps the opening somewhat and may for example be made of the same material as the muffle insert 12. Such covering plates may also have a sealing lip facing the edge of the opening, and it is also possible to fit them from below into the opening 24 respectively present there. In this case, they are reusable, since they can be pulled off as soon as the gypsum-like compound of the muffle has cured.

The muffle insert 12 according to the invention is attached on a muffle base 26, which muffle base acts in a stiffening manner and is designed in such a way that it supports the muffle insert 12 over its surface area from below. For this purpose, the muffle base 26 has a plate 28 made of a plastic that is for example 1 cm thick, on the outer edge of which a groove 30 extends. The groove 30 serves for receiving a projection 22, which is provided on the underside of the collar 22 of the muffle insert 12.

Also belonging to the device for making a muffle 34 is a sleeve 36, which cylindrically surrounds the muffle 34 in a way known per se. The sleeve 36 also overlaps the collar 22 in the downward direction and is supported on a pedestal 38 of the muffle base 26. The overlapping has the effect that the collar 22 is also held against the muffle base 26, so that, with the sleeve 36 uncovered, the muffle base 26 at the bottom insert 12 are undetachably connected to one another.

Figure 2:
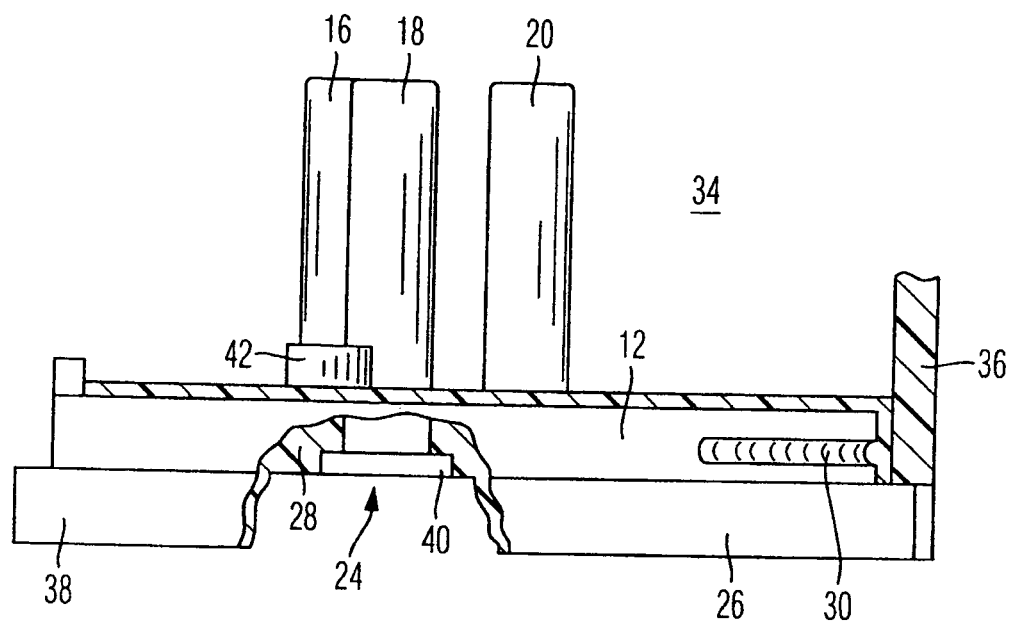
FIG. 2 shows a side view of the device according to FIG. 1.

It can be seen from FIG. 2 that the forming element 18 is configured differently than the forming elements 16 and 20. It is longer and already partly drawn out downward, so that this embodiment is an embodiment in which the forming elements 16-20 are otherwise detachable from the muffle insert. The forming element 18 has a flange 40, which lies against the flat-formed portion 14 from below and is pressed there by the surface-area contact with which the flat-formed portion 14 rests on the muffle base 26. If need be, the relevant forming element 18 may also be omitted and the relevant opening 24 covered by the covering plate mentioned.

An attachment piece 42 can also be seen from FIG. 2. Such an attachment piece is to be seen as an alternative solution for the connection between the forming element and the flat-formed portion 14. This piece is in one piece with the flat-formed portion 14 and, when the forming element is fitted in, is passed through by it.

In the case of this embodiment with such an attachment piece, the muffle insert 12 can also be readily pulled off like a skin after hardening of the muffle compound of the muffle 34, since the shortness of the axial extent of the piece 42 prevents it from anchoring in the material of the muffle 34 to any appreciable extent.

At least the forming elements 16-20 are formed in such a way that they can be burned out without leaving any residual material. This means that they can remain in the cylindrically formed press channels of the muffle 34, but evaporate there. In the case of the embodiment according to FIG. 1, the rest of the muffle insert 12 additionally evaporates, while in the case of the embodiment with the attachment piece 42 the muffle insert 12 can otherwise—that is to say apart from the forming elements—be pulled off, and to that extent is reusable.

The muffle base 26 is in any event not intended for being burned out and is always designed as a reusable element. On the other hand, after curing of the muffle, the sleeve 36 can be peeled off from it in a way known per se, it usually being destroyed in the process.

Figure 3:
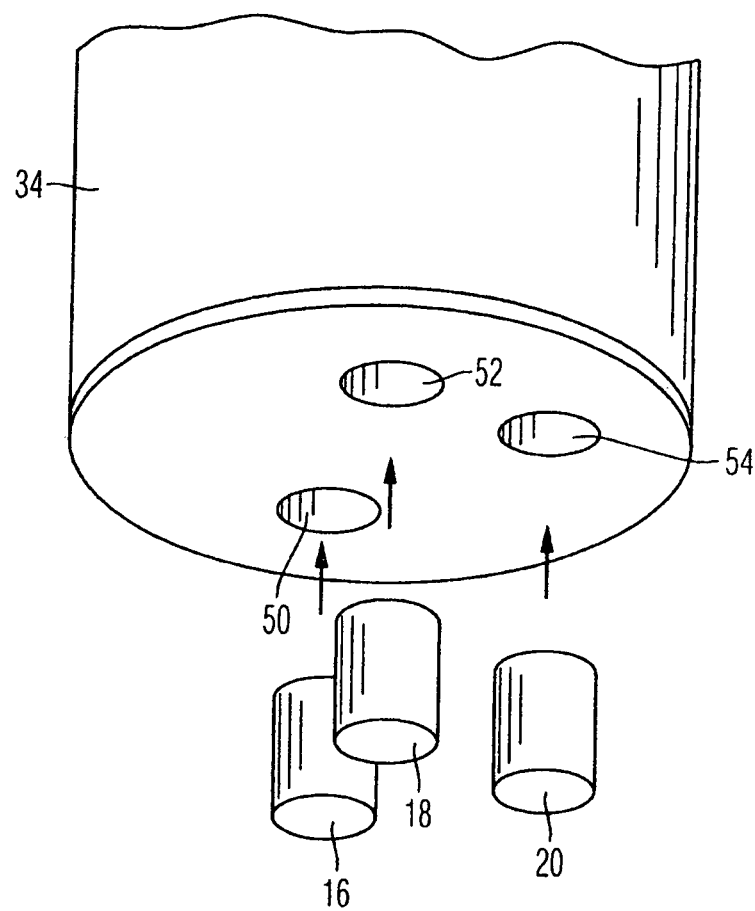
FIG. 3 shows a schematic perspective view of the upper parts of the device according to FIGS. 1 and 2, the muffle additionally being partially represented.

It can be seen from FIG. 3 how the press channels 50, 52 and 54 extend in the muffle 34 once they have been created by the forming elements 16, 18 and 20. Even if the forming elements 16-20 can be burned out, it may in an individual case be succeeded in removing them without leaving any residual material, or at least removing them partially from the press channels 50-54, specifically as a result of the comparatively small wall thickness of the forming elements 16-20.

Figure 4:
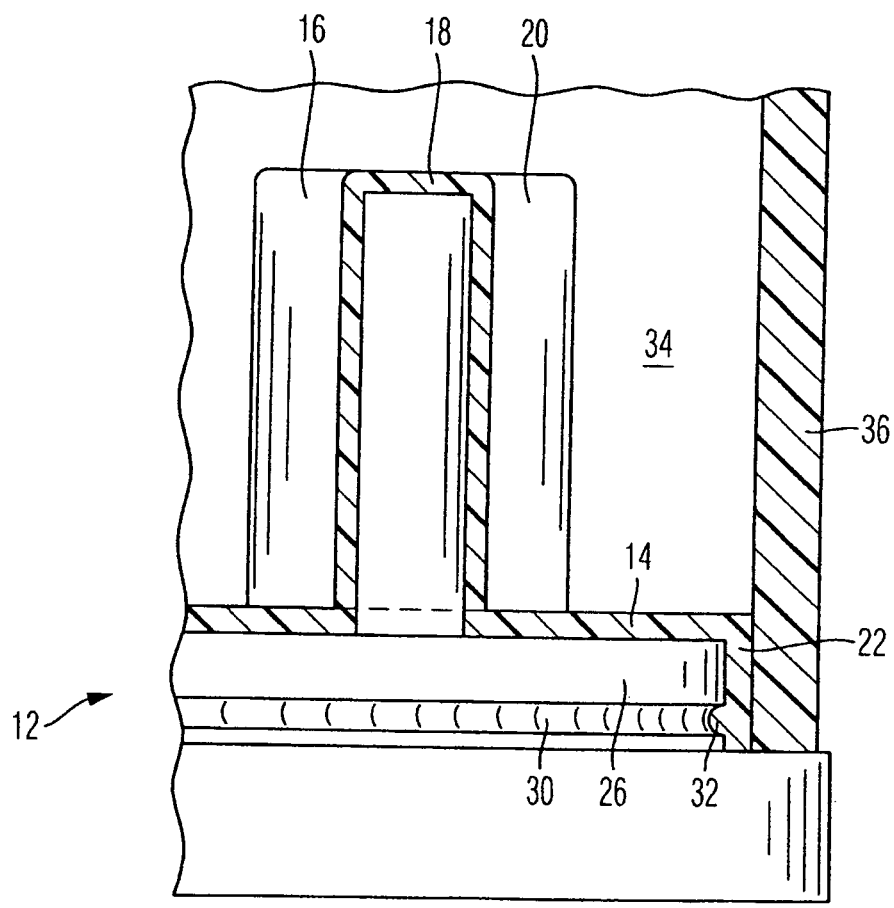
FIG. 4 shows a sectional view of part of the device according to the invention, including part of the muffle and of the sleeve.

How they extend into the muffle 34 can be seen from FIG. 4 in an enlarged representation. They have a somewhat smaller wall thickness than the flat-formed portion 14 of the muffle insert 12 and rest with their underside on the muffle base 26.

Instead of a projection 32, which engages in the groove 30, an annular projection may also be provided, or a corresponding blind-hole bore may be provided in the muffle base 26, intended for the engagement of the projection 32.

It goes without saying that, instead of this, a projection which engages in a corresponding recess on the collar 22 may be provided on the muffle base.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the terms as used in the claims are intended to include not only the designs illustrated in the drawings of this application and the equivalent designs discussed in the text, but are also intended to cover other equivalents now known to those skilled in the art, or those equivalents which may become known to those skilled in the art in the future.

What is claimed is:

1. A device for making a muffle for the manufacture of dental restoration parts by using an embedding compound, the device for making a muffle comprising:
   a muffle base (26),
   a tubular sleeve (36) surrounding the muffle base, and
   at least one muffle insert (12) is a one-piece disposable part which is arranged on the muffle base and can be separated from it,
   wherein at least two cylindrical press-channel forming elements (16, 18, 20) extend from a flat-formed portion (14) of the muffle insert, and further extend parallel to one another and are spaced apart from one another and wherein the forming elements can be burned out leaving no residual material wherein the forming elements have a closed end, at least on one free end face opposite from the flat-formed portion
   wherein the wall thickness of each forming element (16, 18, 20) corresponds to at most 0.1 times the diameter of a forming element (16, 18, 20) and the forming elements (16, 18, 20) have a wall thickness that substantially corresponds to a wall thickness of the flat-formed portion (14);
   wherein the muffle insert (12) protrudes into at least one depression of the muffle base (26) and a projection (32) of the muffle insert (12) protrudes at least partially into a groove (30) on the muffle base (26) formed at least partially around it.

2. The device as claimed in claim 1, wherein the wall thickness of each forming element (16, 18, 20) corresponds to at least 0.03 times the diameter of a forming element (16, 18, 20).

3. The device as claimed in claim 1, wherein the muffle insert (12) is a one-piece disposable part.

4. The device as claimed in claim 1, wherein the muffle base (26) stiffens the muffle insert (12), at least in the region of the flat-formed portion (14), and the forming elements (16, 18, 20) of the muffle insert (12) are supported on the muffle base (26).

5. The device as claimed in claim 1, wherein at least one feed channel for at least one dental restoration part can be attached on the end face opposite from the flat-formed portion (14).

6. The device as claimed in claim 1, wherein the smallest spacing between two cylindrical forming elements (16, 18, 20) is at least 0.5 mm.

7. The device as claimed in claim 1, wherein the flat-formed portion (14) of the muffle insert (12) can be detachably connected to the muffle base (26).

8. The device as claimed in claim 1, wherein the flat-formed portion (14) of the muffle insert (12) can be positively connected to the muffle base (26).

9. The device as claimed in claim 1, wherein the muffle base (26) is formed in a radially elastic manner, at least in the region of the groove (30).

10. The device as claimed in claim 1, wherein a sleeve (36) is fitted onto the muffle base (26) and fixes a part of the flat-formed portion (14) that protrudes into a groove (30) on the muffle base (26).

11. The device as claimed in claim 1, wherein an outside diameter of the flat-formed portion (14) corresponds to an inside diameter of a sleeve (36).

12. The device as claimed in claim 1, wherein the outside diameter of the forming elements (16, 18, 20) is 6 mm to 20 mm.

13. The device as claimed in claim 1, wherein the forming elements (16, 18, 20), are arranged in a circular or square or cruciform or rectangular or arcuate or elliptical manner or in a row, in an inner half of a diameter of the muffle insert (12).

14. The device as claimed in claim 1, wherein the forming elements (16, 18, 20) are formed with different heights and/or have different diameters.

15. The device as claimed in claim 1, wherein the forming elements (16, 18, 20) have a circular form.

16. The device as claimed in claim 1, wherein the forming elements (16, 18, 20) have different outer forms.

17. The device as claimed in claim 1, wherein the forming elements (16, 18, 20) can be fitted with pin shaped elements, having a diameter which corresponds to an inside diameter of the forming element (16, 18, 20) and which are supported on the muffle base (26).

18. The device as claimed in claim 1, wherein the flat-formed portion (14) of the muffle insert (12) can be positively connected to the muffle base (26), by a downwardly extending collar (22).

19. The device as claimed in claim 3, wherein the muffle insert (12) is capable of being free-standing or requires support by one or more pieces in the device.

* * * * *